United States Patent
Kojima et al.

(10) Patent No.: US 10,905,388 B2
(45) Date of Patent: Feb. 2, 2021

(54) PHOTON-COUNTING CT DEVICE, AND CT IMAGING METHOD USING PHOTON COUNTING

(71) Applicant: HITACHI, LTD., Tokyo (JP)

(72) Inventors: Shinichi Kojima, Tokyo (JP); Fumito Watanabe, Tokyo (JP); Yasutaka Konno, Tokyo (JP); Isao Takahashi, Tokyo (JP); Kazuma Yokoi, Tokyo (JP)

(73) Assignee: HITACHI, LTD., Tokyo (JP)

(*) Notice: Subject to any disclaimer, the term of this patent is extended or adjusted under 35 U.S.C. 154(b) by 239 days.

(21) Appl. No.: 16/305,777

(22) PCT Filed: Sep. 8, 2017

(86) PCT No.: PCT/JP2017/032522
§ 371 (c)(1),
(2) Date: Nov. 29, 2018

(87) PCT Pub. No.: WO2018/047950
PCT Pub. Date: Mar. 15, 2018

(65) Prior Publication Data
US 2020/0323502 A1    Oct. 15, 2020

(30) Foreign Application Priority Data
Sep. 12, 2016 (JP) .................. 2016-177672

(51) Int. Cl.
*A61B 6/00* (2006.01)
*A61B 6/02* (2006.01)
*A61B 6/03* (2006.01)

(52) U.S. Cl.
CPC .......... *A61B 6/4241* (2013.01); *A61B 6/025* (2013.01); *A61B 6/032* (2013.01); *A61B 6/4266* (2013.01);
(Continued)

(58) Field of Classification Search
CPC ..... A61B 6/4241; A61B 6/5258; A61B 6/032; A61B 6/482; A61B 6/463; A61B 6/4266; A61B 6/025
(Continued)

(56) References Cited

U.S. PATENT DOCUMENTS 4,788,706 A * 11/1988 Jacobson ............... A61B 6/482
                                                                      250/252.1
9,113,839 B2 * 8/2015 Morton .................. G01N 23/04
(Continued)

FOREIGN PATENT DOCUMENTS

| JP | 2014-079443 A | 5/2014 |
|----|---------------|--------|
| JP | 2014-233633 A | 12/2014 |
| JP | 2016-045202 A | 4/2016 |

OTHER PUBLICATIONS

International Preliminary Report on Patentability dated Mar. 21, 2019 for PCT Application No. PCT/JP2017/032522.
(Continued)

*Primary Examiner* — David P Porta
*Assistant Examiner* — Gisselle M Gutierrez
(74) *Attorney, Agent, or Firm* — Volpe Koenig

(57) ABSTRACT

X-ray photons are counted as to each of energy bands (bins) to which optimum energy ranges are provided, and an image with reduced noise is displayed in a short time. An energy range of at least one of multiple energy bands in an X-ray detector is adjusted, on the basis of a distribution of degrees of X-ray attenuation at respective energy levels, the distribution of degrees of X-ray attenuation being measured in advance with respect to a predetermined direction of a subject. By using the X-ray detector with the energy bands after the adjustment, photon-counting CT imaging is performed.

16 Claims, 12 Drawing Sheets

(52) U.S. Cl.
CPC .............. *A61B 6/463* (2013.01); *A61B 6/482* (2013.01); *A61B 6/5258* (2013.01)

(58) Field of Classification Search
USPC .......................................................... 378/19
See application file for complete search history.

(56) References Cited

U.S. PATENT DOCUMENTS

| | | | |
|---|---|---|---|
| 9,492,134 B2* | 11/2016 | Takasaki | A61B 6/486 |
| 9,820,712 B2* | 11/2017 | Takasaki | A61B 6/481 |
| 2014/0211909 A1* | 7/2014 | Yamazaki | A61B 6/5205 378/4 |
| 2014/0355853 A1 | 12/2014 | Zou et al. | |
| 2015/0355114 A1 | 12/2015 | Taguchi et al. | |
| 2016/0054454 A1 | 2/2016 | Kato et al. | |

OTHER PUBLICATIONS

International Search Report dated Nov. 28, 2017 for the International Application No. PCT/JP2017/032522.

* cited by examiner

FIG. 2
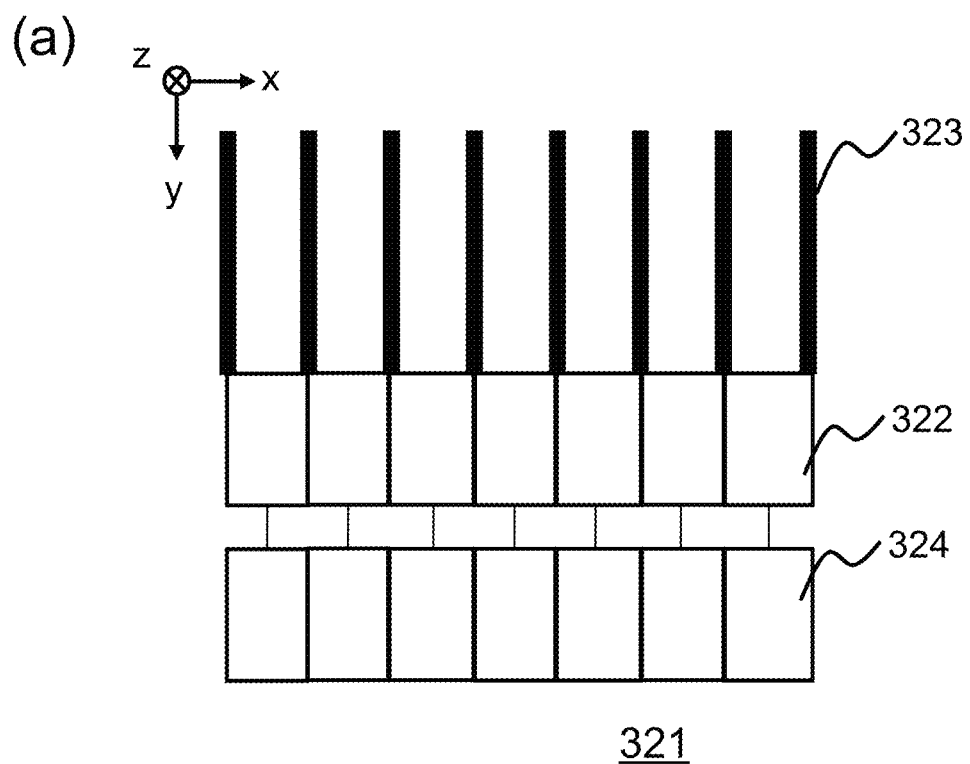
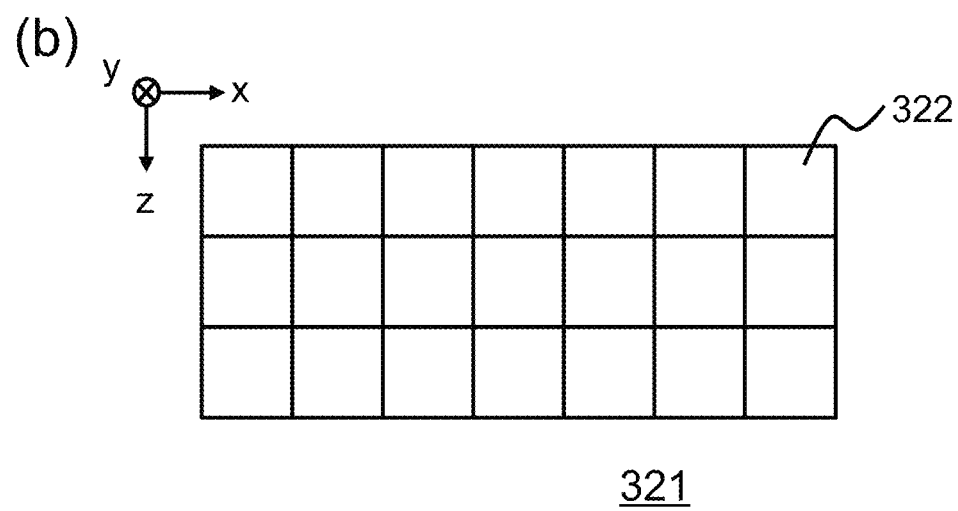

PHOTON-COUNTING CT DEVICE, AND CT IMAGING METHOD USING PHOTON COUNTING

TECHNICAL FIELD

The present invention relates to an X-ray CT (Computed Tomography) device having a photon-counting (photon counting) mode (hereinafter, referred to as PCCT device). More particularly, the present invention relates to a technique for reducing statistical noise on the low-energy side of the PCCT device.

BACKGROUND ART

An X-ray CT device acquires X-ray transmission data of a subject, while rotating a pair of an X-ray source and an X-ray detector around the subject, keeping the positional relationship of the X-ray source and the X-ray detector opposed to each other placing the subject therebetween, and performs calculations to reconstruct a computed tomography image (CT image) of the subject. This X-ray CT device may serve as an industrial and security-use inspection system, or a medical diagnostic imaging device.

A PCCT device equipped with a photon counting mode is one of such medical X-ray CT devices. In the PCCT device, a photon counting type detector counts photons of X-rays (X-ray photons) that have passed through a subject, as to each detecting element. This configuration allows, for example, acquisition of a spectrum that enables estimation of elements constituting internal tissue of the subject, through which X-rays have passed, and an X-ray CT image on which element-level differences are depicted in detail can be obtained.

The PCCT device categorizes individual X-ray photons being counted, according to energy values, and then X-ray intensity can be obtained on the basis of energy band (energy bin). In some cases, by utilizing the feature above, the PCCT device may extract X-rays only within a specific energy range, for reconstructing an image to be used for diagnosis.

In the X-ray CT device as described above, the X-ray source is made to turn around the subject, so that images of the subject are taken at various angles. However, X-rays are likely to attenuate significantly, when passing through inside of the subject; such as a part including many bones, and a part with locally embedded metal like a pacemaker. A maximum X-ray energy of the X-rays is 120 keV, for example, in the imaging at 120 kVp (120 kV peak imaging), but the X-rays further include energy equal to or less than this energy level, and thus forming an energy distribution. X-rays on the low energy side are likely to attenuate more drastically within the subject, relative to the X-rays on the high energy side. Therefore, the number of detected signals on the low energy side is drastically reduced in the parts including many bones or metal within the subject. In particular, in the case of the PCCT device, counts in energy bins (the number of X-ray photons) on the low energy side become extremely small, causing image quality degradation.

In order to avoid the foregoing problems, for example, Patent Document 1 discloses a technique where X-ray photon counts in energy bins, being small in number, is combined with the X-ray photon counts in an adjacent energy bin, and an image is reconstructed using output signals from thus combined energy bins. With this configuration, the image is less affected by noise that is likely to be delivered on the output signals from the energy bins with a small number of X-ray photon counts.

PRIOR ART DOCUMENT

Patent Document

Patent Document 1
Japanese Unexamined Patent Application Publication No. 2014-233633

DISCLOSURE OF THE INVENTION

Problems to be Solved by the Invention

According to the technique disclosed by the Patent Document 1, the number of X-ray photons that have passed through an object is counted in each of at least three bins; a low energy bin, a middle energy bin, and a high energy bin. Then, the count of the X-ray photons in the middle energy bin is added to the count in the low energy bin, when ray paths of the X-rays are long and most of the low energy photons are absorbed by the object. On the other hand, for short ray paths, the count in the middle energy bins is added to the count in the high energy bin (paragraph 0035). In other words, the technique described in the Patent Document 1 has a configuration that a PCCT device takes an image of the object, acquires the count in each of the energy bins, determines two energy bins to be combined, on the basis of thus obtained counts, a material noted by an operator, scanning conditions, and others. Then, an image is reconstructed using the count after combined. Therefore, the energy bins to be combined are selected on the basis of the count, and other information, and it is not envisaged to change the energy bins to be combined, even when noise reduction is insufficient in the reconstructed image. If the energy bins to be combined are changed, this may cause redoing of the image reconstruction, and it takes time for displaying an image. In the case where noise reduction is insufficient in the reconstructed image, it is conceivable to change the scanning conditions, followed by imaging the object again by the PCCT device. However, this may cause increased X-ray exposure for the object, also taking time for obtaining a desired image, resulting in that burdens are placed on both the object and the operator.

An objective of the present invention is to count X-ray photons as to each of the energy bands (bins) having an optimum energy range, and to display an image with reduced noise in a short time.

Means for Solving the Problems

In order to achieve the foregoing objective, according to the present invention, there is provided a photon-counting device as described below. The photon-counting device includes, an X-ray emitter configured to irradiate a subject with X-rays, an X-ray detector configured to count a plurality of X-ray photons passing through the object, with discriminating the X-ray photons into multiple energy bands in response to energy levels of the X-ray photons, a rotator configured to rotate the X-ray emitter and the X-ray detector around the subject, and an energy band setter configured to set the energy bands in the X-ray detector. The energy band setter sets an energy range of at least one of the plurality of the energy bands in the X-ray detector, on the basis of a distribution of degrees of X-ray attenuation at respective energy levels, which is measured in advance with respect to a predetermined direction on the subject.

Advantage of the Invention

According to the present invention, the X-ray photons are counted as to each of the energy bands (bins) that are provided with optimum energy ranges, allowing an image with reduced noise to be displayed in a short time.

BRIEF DESCRIPTION OF THE DRAWINGS

FIG. 2(a) is a side view and FIG. 2(b) is a top view of the X-ray detector of the present embodiment;

BEST MODE FOR CARRYING OUT THE INVENTION

Figure 1:
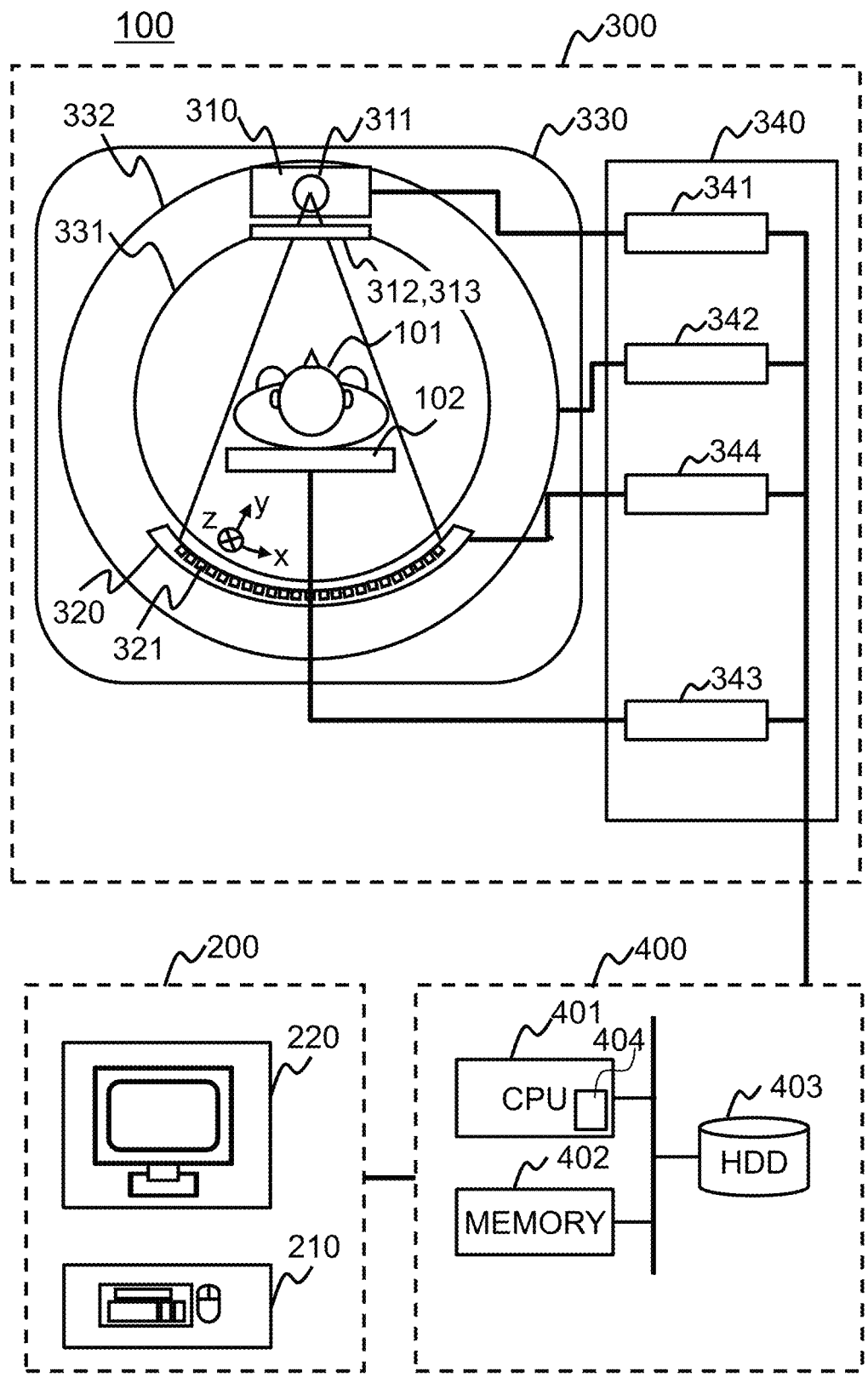
FIG. 1 is a block diagram showing a configuration of the photon-counting CT device according to an embodiment of the present invention.

There will now be described an example of a photon-counting CT device of an embodiment according to the present invention. Hereinafter, in all the figures illustrating the embodiments of the present invention, components with an identical function are labeled with the same reference numeral, and they will not be redundantly explained.

The photon-counting CT device (PCCT device) of the present embodiment has a configuration for setting an energy range of at least one of multiple energy bands in an X-ray detector, on the basis of a distribution of degrees of X-ray attenuation at predetermined multiple energy levels, the distribution being measured in advance with respect to a predetermined direction of the subject. With this configuration, the X-ray photons are counted as to each of the energy bands (bins) that are provided with optimum energy ranges, respectively, allowing a CT image with reduced noise to be displayed in a short time.

Figure 3:
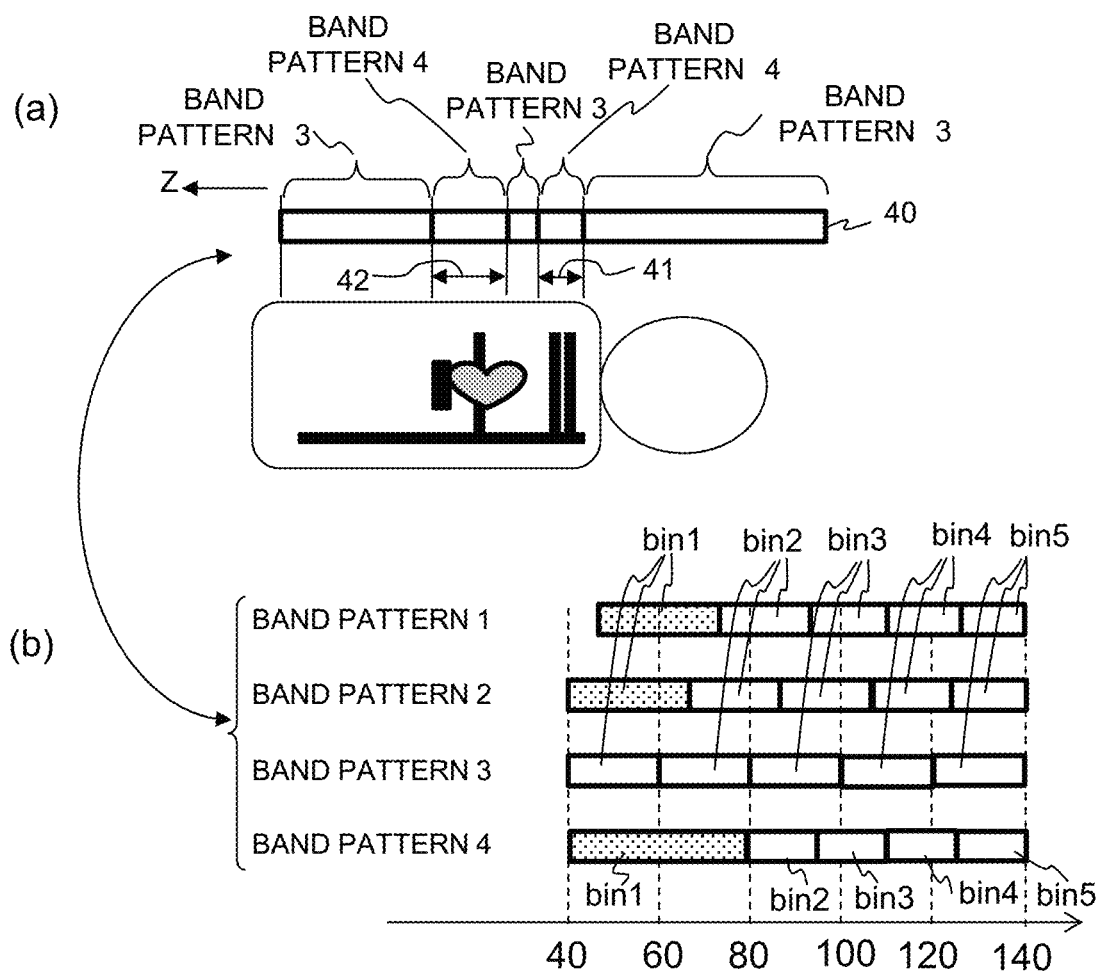
FIG. 3(a) illustrates energy band patterns are set for respective sections in the z-axis (body axis) direction.
FIG. 3(b) illustrates an example of various types of the energy band pattern in the present embodiment.

With reference to FIGS. 1 to 3, there will now be described an overview of the PCCT device of the present embodiment. The PCCT device of the present embodiment, an overall configuration thereof being illustrated in FIG. 1, includes an X-ray emitter 310 for irradiating a subject 101 with X-rays, an X-ray detector 321, a rotator (rotating panel) 332 for rotating the X-ray emitter 310 and the X-ray detector 321 around the subject, and an energy band setter 404.

The X-ray detector 321 is not a conventional integrator type (current-mode measurement system), but a photon-counting type detector. In other words, the X-ray detector 321 discriminates a plurality of X-ray photons passing through the subject 101, into multiple energy bands in response to energy levels of the X-ray photons, and counts the X-ray photons as to each energy band. By way of example, as shown in FIG. 2, the X-ray detector 321 comprises a plurality of detecting elements 322 in an array, and counter circuits 324. The detecting element 322 detects X-ray photons, and outputs electrical signals in response to energy levels of the X-ray photons. The counter circuit 324 discriminates the electrical signals into multiple energy bands in response to the energy levels, and counts the signals as to each energy band.

The energy band setter 404 sets an energy range of at least one of the multiple energy bands in the X-ray detector 321, on the basis of the distribution of degrees of X-ray attenuation at respective energy levels, the distribution being measured in advance with respect to a predetermined direction of the subject 101. For example, as shown in FIG. 3(a), in a section (region) 41 including many bones or in a section (region) 42 embedded with metal, within the subject 101, there is a high degree of attenuation in low-energy level X-rays. Thus, the number of X-ray photons of low-energy level reaching the X-ray detector 321 through such regions becomes small. Therefore, the number of X-ray photons of low-energy level, counted by the X-ray detector 321, also becomes small. In the present embodiment, for example, in the sections (regions) 41 and 42 including an energy level with the degree of X-ray attenuation higher than a predetermined threshold in the distribution of degrees of X-ray attenuation 40, the energy band setter 404 expands the energy width of the energy band (bin 1 of FIG. 3(b)) including the energy level with such high degree of X-ray attenuation among the multiple energy bands (bins 1 to 5) in the X-ray detector 321, to be larger than the other bands (bins 2 to 5) (band patterns 1, 2, and 4). Specifically, the energy band setter 404 makes adjustments to expand the energy width of the energy band (bin 1 in FIG. 3(b)) including the energy level with the high degree of X-ray attenuation, among the multiple energy bands in the counter circuit 324. Accordingly, this allows increase of the number of the X-ray photons counted in the energy band (bin 1) including the energy level with the high degree of attenuation, and thus, a level of detected signals is raised, resulting in less affected by noise. It is to be noted taking a scanogram by the PCCT device enables acquisition of the distribution of degrees of X-ray attenuation 40, which will be described below. For this case, if there is another energy level with the degree of X-ray attenuation higher than a predetermined threshold, the energy band setter 404 may make adjustments so that the energy width of the energy band (bin 1 in FIG. 3(b)) is expanded larger than the energy width of the energy band (bin 1) including that energy level, the energy width previously provided at the time of obtaining the distribution of degrees of X-ray attenuation 40.

It is further possible to provide predetermined multiple types of energy band sets (referred to as "patterns" in the following, and band patterns 1 to 4 are shown in FIG. 3(b)). The energy band setter 404 may select and set in the X-ray detector 321, one energy band pattern (in this example, the band pattern 4), in response to the distribution of degrees of X-ray attenuation. This configuration facilitates adjustment of the energy width of the energy band.

The PCCT device of the present embodiment is further provided with a movable unit (table) 102 for moving the subject 101 in the direction crossing (orthogonal to) a rotating plane of the rotator 332. In this case, the energy band setter 404 sets multiple sections in the moving direction (body axis direction) of the movable unit 102, and the energy band setter is able to set, as to each of the multiple sections, a different width of energy range for at least one of the multiple energy bands. For example, as shown in FIG. 3 (a), the energy band setter 404 selects and sets an optimum pattern, out of the band patterns 1 to 4, in the body axis direction.

In addition, the energy band setter 404 may change the energy range of at least one energy band, among the multiple energy bands in the X-ray detector 321, in response to the rotation angle of the rotator 332. In this case, the distribution of degrees of X-ray attenuation 40 is acquired in advance as to each of multiple directions of the subject 101. The energy band setter 404 sets the energy range of the energy band, in response to the rotation angle of the rotator 332, on the basis of the distributions of degrees of X-ray attenuation 40 in the multiple directions.

It is to be noted that obtaining a scanogram by the PCCT device enables acquisition of the distribution of degrees of X-ray attenuation 40. For example, the X-ray emitter 310 irradiates the subject 101 with X-rays without rotating the rotator 332, and the X-ray detector 321 with predetermined values of energy ranges respectively for the multiple energy bands, counts the X-ray photons passing through the subject 101, thereby obtaining the scanogram that indicates the distribution of degrees of X-ray attenuation 40. In this situation, the subject 101 is moved in the direction crossing (e.g., orthogonal to) the rotating plane of the rotator 332, whereby the distribution of degrees of X-ray attenuation 40 can be obtained for each of slices that are parallel to the rotating planes respectively at a plurality of positions in the body axis direction of the subject 101. The distribution of degrees of X-ray attenuation 40 may be obtained from measurement by a device other than the PCCT device that performs CT imaging.

<Specific Configuration of the Photon-Counting CT Device>

There will now be specifically described the PCCT device 100 of the present embodiment.

With reference to FIG. 1, a specific configuration of the PCCT device of the present embodiment will be described. As illustrated in FIG. 1, the PCCT device 100 of the present embodiment comprises a UI unit 200, a measurement unit 300, and an arithmetic unit 400.

The UI unit 200 accepts an input from a user, and presents to the user, a result of processing by the arithmetic unit 400. Therefore, the UI unit 200 is provided with an input device 210 such as a keyboard and a mouse, and an output device 220 such as a display device (monitor) and a printer. The display device may comprise a liquid crystal display, a CRT (Cathode Ray Tube), or the like. The display device may be configured to have a touch panel function that enables usage as the input device 210.

According to the control by the arithmetic unit 400, the measurement unit 300 irradiates the subject 101 with X-rays, and measures X-ray photons passing through the subject 101. The measurement unit 300 is provided with a gantry 330, a controller 340, and a table (movable unit) 102 for placing the subject 101 thereon, in addition to the aforementioned X-ray emitter 310 and the X-ray detect device 320. The controller 340 comprises a radiation controller 341, a gantry controller 342, a table controller 343, and a detection controller 344.

[Gantry]

At the center of the gantry 330, there is provided a circular opening 331 for placing the subject 101 and the table 102. There are provided inside the gantry 330, a rotating panel 332 equipped with the X-ray emitter 310 and the X-ray detector 321, and a drive mechanism for rotating the rotating panel 332. The rotating panel 332 is provided with notches (not illustrated) for controlling measurement time in the rotational direction, and when a notch intersects a sensor (not illustrated), the gantry controller 342 delivers a signal to the detection controller 344. Then, the detection controller 344 issues to the X-ray detect device 320, a command instructing to output data that is counted so far by the counter circuit 324 of the X-ray detector 321, as data associated with an angle of 1 degree. The diameter of the opening 331 of the gantry 330 is 700 mm. Distance between an X-ray generation point of the X-ray tube 311 and an X-ray incident plane of the X-ray detector 321 is 1,000 mm, for instance.

The time required for one revolution of the rotating panel 332 is set by a parameter entered by the user via the UI unit 200. In the present embodiment, the required time for revolution is assumed as 1.0 second per imaging time. The number of imaging times per revolution, performed by the measurement unit 300, is set to 900, for instance, and every time the rotating panel 332 rotates 0.4 degrees, one imaging is performed, that is, counted data from the counter circuit 324 is outputted. The aforementioned requirements are not limited to the values as described above, and they may be variable according to configurations of the PCCT device 100.

In the following descriptions, it is assumed that the circumferential direction of the opening 331 is x-direction, and a radial direction is y-direction. The direction orthogonal to the x-direction and the y-direction is assumed as z-direction (generally, a body-axis direction).

[X-ray emitter]

The X-ray emitter 310 emits X-rays, and irradiates the subject 101 with thus emitted X-rays. The X-ray emitter 310 is provided with an X-ray tube 311, an X-ray filter 312, and a bowtie filter 313.

The X-ray tube 311 irradiates the subject 101 with X-ray beams, using high voltage that is supplied under the control of the radiation controller 341. The X-ray beams thus radiated spread at a fan angle and a cone angle. The subject 101 is irradiated with the X-ray beams, along with revolution of the rotating panel 332 in the gantry 330.

The X-ray filter 312 controls the amount of X-rays emitted from the X-ray tube 311. In other words, the X-ray filter changes a spectrum of the X-rays. The X-ray filter 312 of the present embodiment attenuates the X-rays emitted from the X-ray tube 311, so that the X-rays applied to the subject 101 from the X-ray tube 311 provide a predetermined energy distribution. The X-ray filter 312 is used to optimize an exposure dose given to the subject 101, being a patient. Therefore, it is designed to intensify the exposure dose in an energy band that is necessary.

The bowtie filter 313 is provided to reduce the exposure dose in the periphery. Using a feature that a slice of a human body, being the subject 101, has an oval shape, the bowtie filter is employed to optimize the exposure dose by intensifying the exposure dose around the center and reducing the exposure dose on the periphery.

[X-Ray Detect Device]

The X-ray detect device 320 has a configuration that multiple X-ray detectors 321 are placed in an arc-like form. As shown in FIGS. 2(a) and 2(b), the X-ray detector 321 is provided with collimators 323, which are placed respectively on the detecting elements 322, so as to restrict the incident direction onto the X-ray detector 321, in addition to the aforementioned plurality of detecting elements 322 and counter circuits (hereinafter, referred to as counting circuits) 324. In the examples of FIGS. 2(a) and 2(b), the detecting elements 322 are arranged two-dimensionally.

The detecting element 322 converts the incident X-ray photons into charge signals, in proportion to the energy of the X-ray photons. By way of example, CdTe (cadmium telluride)-system semiconductor element may be used as the detecting element 322. It is to be noted that a scintillator that emits fluorescence upon receiving the X-rays and a photo diode that converts the fluorescence to electricity may also be used as the detecting element 322.

Figure 4:
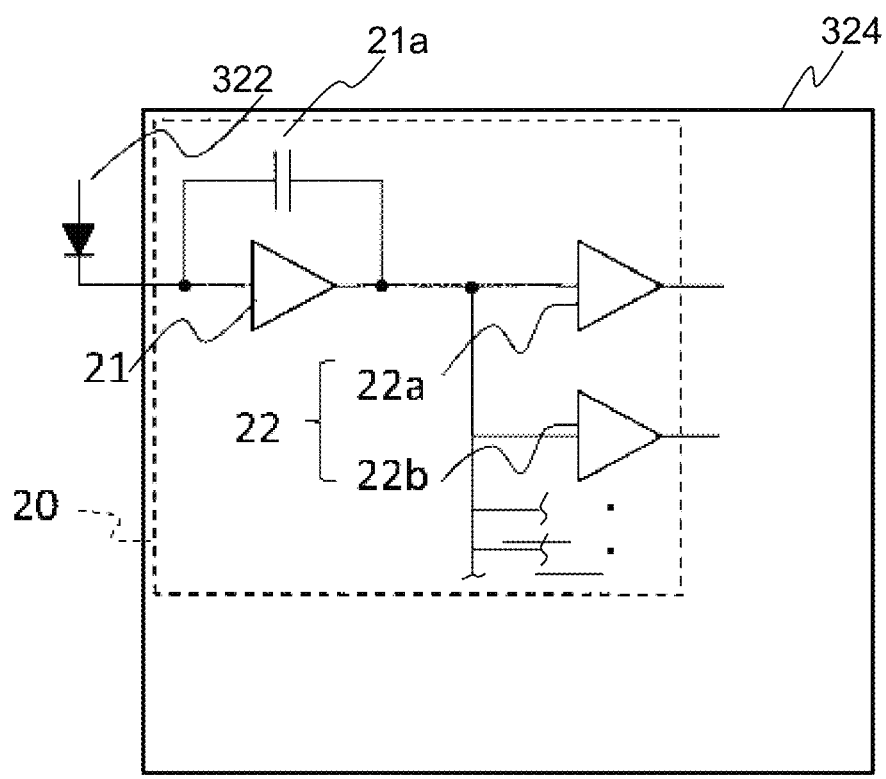
FIG. 4 is a circuitry diagram showing one example of a count circuit in the present embodiment.

The counting circuit 324 converts the charge signal outputted from each of the detecting elements 322 into an electrical signal (analogue signal) for one pulse, as to each of the X-ray photon, and the electrical signals are discriminated into any of multiple energy bands, in response to an energy level of the electrical signal, and then counted. Specifically, as shown in FIG. 4, the counting circuit 324 is provided with a readout circuit block 20, and the readout circuit block 20 comprises a charge amplifier 21, a feedback capacitance 21a connected in parallel with the charge amplifier 21, and a plurality of comparators 22 (22a, 22b, and so on). The number of the plurality of comparator 22a, 22b, and so on, corresponds to the number of a predetermined number of energy bands (bins).

Each of the detecting elements 322 is connected to the charge amplifier 21 within the readout circuit block 20. The charge amplifier 21 uses the feedback capacitance 21a to convert the charge signals outputted from the detecting element 322, into voltage signals. The detecting element 322 generates the electric charge that is proportional to the energy of the incident X-ray photons, and a crest value outputted from the charge amplifier 21 is proportional to the energy of the X-ray photons. In order to prevent the build-up of electric charge in the feedback capacitance 21a, the feedback capacitance 21a is connected to a switch that resets the electric charge, or connected to a resistance that discharges the built-up electric charge.

The output side of the charge amplifier 21 is connected to more than one comparator 22 (22a, 22b, and so on). There are provided in the comparators 22a, 22b, and so on, respectively, voltage output units for outputting comparable voltages different from one another. The comparators such as 22a and 22b issue trigger signals, when the crest value of the voltage signal outputted from the charge amplifier 21 exceeds the comparable voltage being a threshold. Since the thresholds (comparable voltages) inputted respectively in the comparators such as 22a and 22b are different from one another, for example, when the threshold of the comparator 22b is higher than the threshold of the comparator 22a, and the crest value of the voltage signal outputted from the charge amplifier 21 is higher than the threshold of the comparator 22a, and equal to or lower than the threshold of the comparator 22b, only the comparator 22a issues the trigger signal. On the other hand, when the crest value of the voltage signal outputted from the charge amplifier 21 exceeds the thresholds of both the comparator 22a and the comparator 22b, both the comparators 22a and 22b issue the trigger signals. Then, it is determined which comparators have outputted the trigger signals, out of the plurality of comparators 22 (22a, 22b, and so on), and a circuit (not illustrated) for counting the trigger signals is provided, which allows categorization of the energy values of X-ray photons into the energy bands, and counting the X-ray photons as to each of the energy bands.

At this time, the detection controller 344 sets voltage values of the comparable voltages of the comparators 22 (22a, 22b, and so on), in response to an instruction from the energy band setter 404, thereby adjusting the energy width of the energy band.

Alternatively, an ADC (Analog-to-Digital Converter) and a DAS (Data Acquisition System) may be provided, instead of the comparators 22, for counting the voltage signals of the charge amplifier 21, as to each of the energy bands. Also in this case, the detection controller 344 may control the DAS in response to an instruction from the energy band setter 404, whereby the energy width of the energy band can be adjusted.

The band pattern 3 as shown in FIG. 3(b) is a pattern example where the energy range from the minimum energy 40 keV to the maximum energy 140 keV is divided by energy width $\Delta B=20$ keV, into 5 energy bands (bins 1 to 5). That is, bin 1 is set to the energy range from 40 to 60 keV, bin 2 is set to the energy range from 60 to 80 keV, bin 3 is set to the energy range from 80 to 100 keV, bin 4 is set to the energy range from 100 to 120 keV, and bin 5 is set to the energy range from 120 to 140 keV. As for the band pattern 2, the energy width of bin 1 is made larger than the bin 1 of the band pattern 3, and the remaining energy ranges are divided equally into four bands (bins 2 to 5). As for the band pattern 1, the minimum energy is changed to 45 keV, and the overall energy range is made narrower than the band pattern 2, and further, the energy width of bin 1 is made larger than the band pattern 3, and the remaining energy ranges are divided equally into four bands (bins 2 to 5). As for the band pattern 4, the energy width of bin 1 is still larger than the band pattern 2, and the bin 1 is set to the energy range from 40 to 80 keV, the bin 2 is set to the energy range from 80 to 95 keV, the bin 3 is set to the energy range from 95 to 110 keV, the bin 4 is set to the energy range from 110 to 125 keV, and the bin 5 is set to the energy range from 125 to 140 keV.

Count results of the respective energy bands are inputted in the arithmetic unit 400.

By way of example, the number (channel number) of the detecting elements 322 of the X-ray detector 321 is 1,000. The size of each detecting element in the x-direction is 1 mm, for instance.

For ease of manufacturing, the X-ray detect device 320 may be configured such that the X-ray detector 321 has a planar shape, and a plurality of X-ray detectors 321 are arranged in a pseudo arc in a manner that the centers of the planes are positioned on the arc.

[Controller]

As described above, the controller 340 includes the radiation controller 341, the gantry controller 342, the table controller 343, and the detection controller 344. The radiation controller 341 controls radiation of X-rays from the X-ray tube 311. The gantry controller 342 controls drive of rotation of the rotating panel 332. The table controller 343 controls drive of the table 102. The detection controller 344 controls X-ray detection in the X-ray detector 321. Though not illustrated, there may be provided time-measurement equipment for measuring the time in the rotation direction. When a signal generated at the time the notch of the rotating panel 332 intersects the sensor enters the detection controller 344, the time measurement equipment simultaneously receives thus generated signal, and stores the measurement time in the rotation direction.

While CT imaging is performed, the gantry controller 342 rotates the rotating panel 332, and moves the table 102 in the normal direction of the rotating plane of the rotating panel 332 (z-direction: in general, body axis direction). With this configuration, the X-ray emitter 310 irradiates the subject 101 with X-rays, from various directions, with turning around the subject 101. The X-ray detector 321 detects the X-ray photons passing through the subject 101, and discriminate the detected signals into the energy bands in response to the energy levels, and count the X-ray photons as to each energy band. On the other hand, in the scanogram imaging, the gantry controller 342 does not rotate the rotating panel 332, and moves only the table 102 in the z-direction for one time. With this configuration, the X-ray emitter 310 irradiates the subject 101 with X-rays, from a predetermined direction. The X-ray detector 321 detects the X-ray photons passing through the subject, discriminates the detected signals into the energy bands in response to the energy levels, and counts the X-ray photons as to each of the energy bands. After obtaining the scanogram with respect to one direction, the direction for applying the X-rays may be changed as required (e.g., the rotation panel 332 is turned by 90 degrees), whereby scanograms can be obtained in multiple directions.

[Arithmetic Unit]

Figure 5:
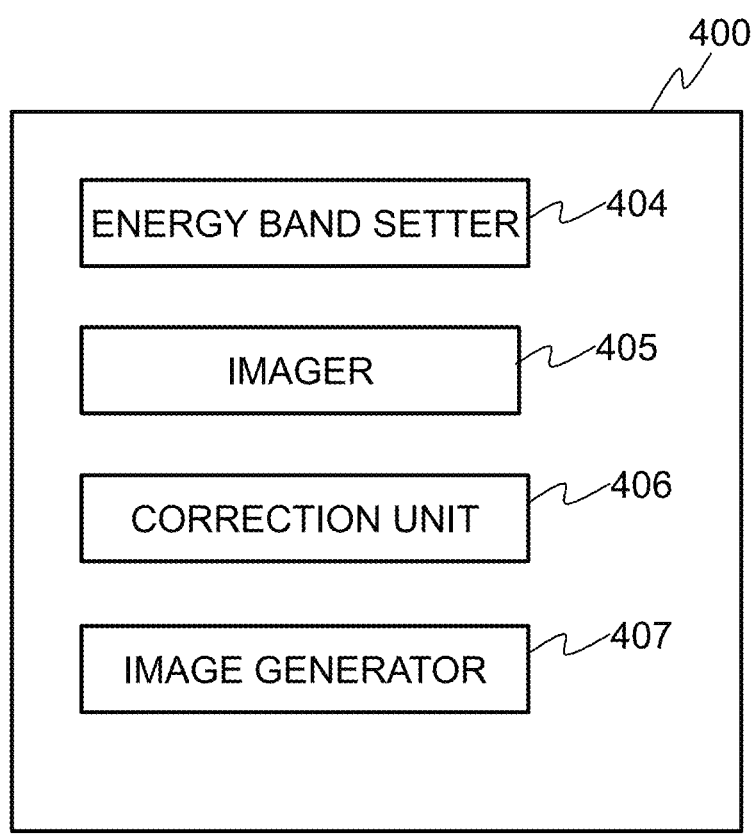
FIG. 5 is a functional block diagram of an arithmetic unit 400 in the present embodiment.
Figure 6:
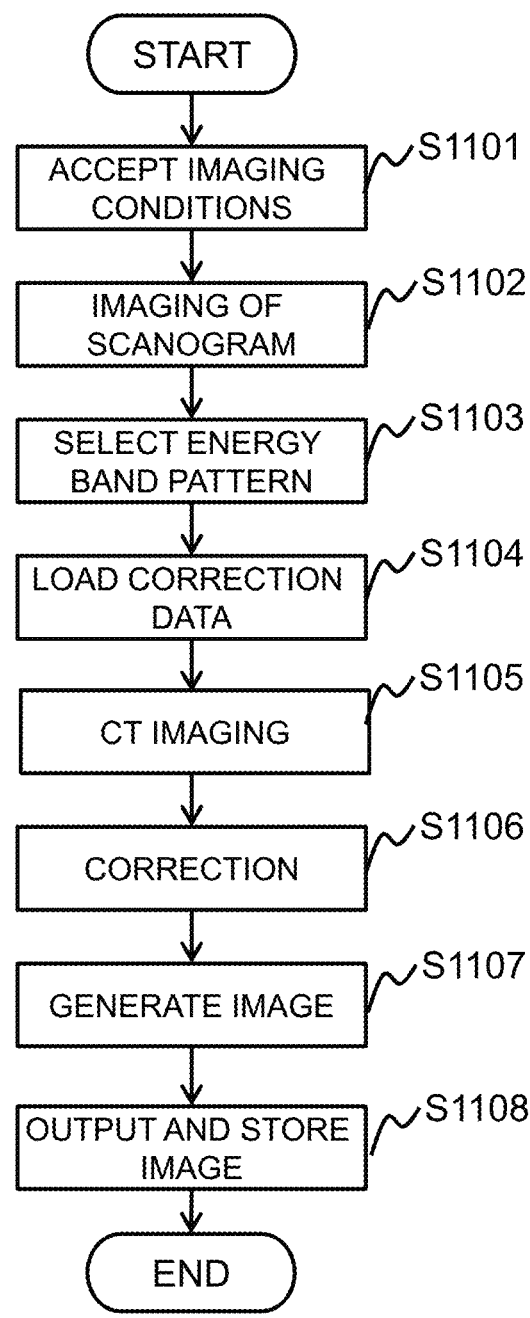
FIG. 6 is a flowchart showing an imaging process of the present embodiment.

The arithmetic unit 400 controls overall operations of the PCCT device 100 and processes the data acquired by the measurement unit 300, thereby executing the imaging. The arithmetic unit 400 is provided with a central processing unit (CPU) 401, a memory 402, and an HDD (Hard disk drive) unit 403. As indicated by the functional block diagram of FIG. 5, the arithmetic unit 400 has functions of an energy band setter 404, an imager 405, a correction unit 406, and an image generator 407. For example, the CPU 401 loads programs held in advance in the HDD unit 403 into the memory 402 and executes the programs, so as to perform imaging process as shown in FIG. 6, whereby each of the functions above can be implemented by software.

All or a part of the functions of the arithmetic unit 400 may be implemented, for example, by an integrated circuit such as ASIC (Application Specific Integrated Circuit) and FPGA (Field Programmable Gate Array).

The energy band setter 404 sets appropriately, the energy bands for the counting circuit 324 of the X-ray detector 321, on the basis of the distribution of degrees of X-ray attenuation 40 at respective energy levels, acquired in advance by the scanogram imaging, or the like. The imager 405 executes imaging such as CT imaging and scanogram imaging. The correction unit 406 performs a correction process on the count data as to each of the energy bands, the data being collected by the X-ray detect device 320, under the control of the detection controller 344. The correction process here may include, for example, linearity correction by a reference correction circuit, a logarithmic transformation process, an offset process, a sensitivity correction, and a beam hardening correction, a water phantom calibration, and a CT value correction. The image generator 407 reconstructs an X-ray CT image, from the count information after the correction that is applied by the correction unit 406. For example, the image generator 407 applies logarithmic transformation to the number of the X-ray photons, and then, performs image reconstruction, by using various publicly known methods such as FeldKamp method and successive approximation. In order to generate an image, projection data stored in all the energy bins may not be used, but only the count in predetermined energy bands may be used for performing the image reconstruction.

The HDD unit 403 stores data items, such as data used for the processing, data generated during the processing, and data obtained as a result of the processing. The result of the processing may be delivered to the output device 220 in the UI unit 200.

[UI Unit]

The UI unit 200 accepts an imaging condition from a user, and delivers the imaging condition to the arithmetic unit 400. By way of example, the UI unit 200 displays an acceptance screen on the monitor, for accepting imaging conditions, and the user enters the imaging conditions, via the acceptance screen, by using a mouse, a keyboard, and a touch panel, for instance. The imaging conditions to be provided may include, for example, tube current of the X-ray tube 311, tube voltage, an imaging region of the subject 101, a shape of the X-ray filter 312, a shape of the bowtie filter 313, and optical resolution. The user may not necessarily enter the imaging conditions every time. For example, typical imaging conditions are stored in advance, and they may be read out when used.

[Imaging Process Flow]

Next, with reference to FIG. 6, there will be described an imaging processing flow of the present embodiment according to the arithmetic unit 400. FIG. 6 shows a processing flow of the imaging executed by each of the functions of the arithmetic unit 400. In the example of the imaging process shown in FIG. 6, the distribution of degrees of X-ray attenuation 40 is acquired by obtaining a scanogram in the imaging process.

Firstly, the imager 405 of the arithmetic unit 400 accepts an input of imaging conditions from a user via the UI unit 200 (step S1101). The input of the imaging condition being accepted may include, for example, tube voltage, tube current, thickness and shape of the X-ray filter 312, and a shape of the bowtie filter 313.

Next, the imager 405 obtains a scanogram depicting the distribution of degrees of X-ray attenuation 40 of the subject 101 (step S1102). The imager 405 instructs the table controller 343 to move the table 102, in the direction perpendicular to the rotating panel 332, and also instructs to stop the movement when the imaging position of the rotating panel 332 coincides with a designated imaging position. Then, positioning of the subject 101 is completed. Next, the imager 405 instructs the table controller 343 to move the table 102 at a predetermined speed, but no command is given to the gantry controller 342. Accordingly, the rotating panel 332 does not rotate, and only the table 102 moves to the X-ray detector 321. In this situation, the imager 405 gives the radiation controller 341 an instruction of X-ray emission timing from the X-ray tube 311, and gives the detection controller 344 an instruction of imaging timing by the X-ray detector 321. In response to those instructions, the X-ray emitter 310 applies X-rays, and the X-ray detector 321 counts the X-ray photons as to each of the energy bands, having a predetermined band pattern (e.g., the band pattern 3 in FIG. 3 (b)). Then, under the control of the detection controller 344, the X-ray detector 321 outputs count data to the arithmetic unit 400, every 1 ms, for instance. Accordingly, the count data of the X-ray photons passing through the subject 101 as to each of the energy bands in the slice direction is acquired as a scanogram. Taking the scanogram is repeated as to each slice, until the table reaches a distance designated by the user, or a moving limit distance of the table 102.

The arithmetic unit 400 allows the correction unit 406 to perform correction as required, on the count data (scanogram) of the X-ray photons in every energy band as to each slice, and stores in the HDD 403, the corrected count data as the distribution of degrees of X-ray attenuation 40.

If necessary, the X-ray irradiation range in the z-direction may be restricted. Methods for restricting the irradiation range in the z-direction may include, for example, a method for turning on and off the voltage application to the X-ray tube, and a method for providing a shutter to attenuate and absorb X-rays before reaching the X-ray tube, and controlling the X-rays by turning on and off the shutter. In addition, the rotating panel 332 may be rotated by 90 degrees, for example, thereby generating a plurality of scanograms as required, by irradiation of X-rays at different angles.

Next, the energy band setter 404 employs the scanogram obtained in step S1102 as the distribution of degrees of X-ray attenuation 40, and sets the energy bands in the X-ray detector 321, for the CT imaging of step S1105 performed later (step S1103). There are stored predefined multiple types of energy band patterns in the HDD 403, and the energy band setter 404 selects and sets an optimum pattern in the X-ray detector 321.

Figure 7:
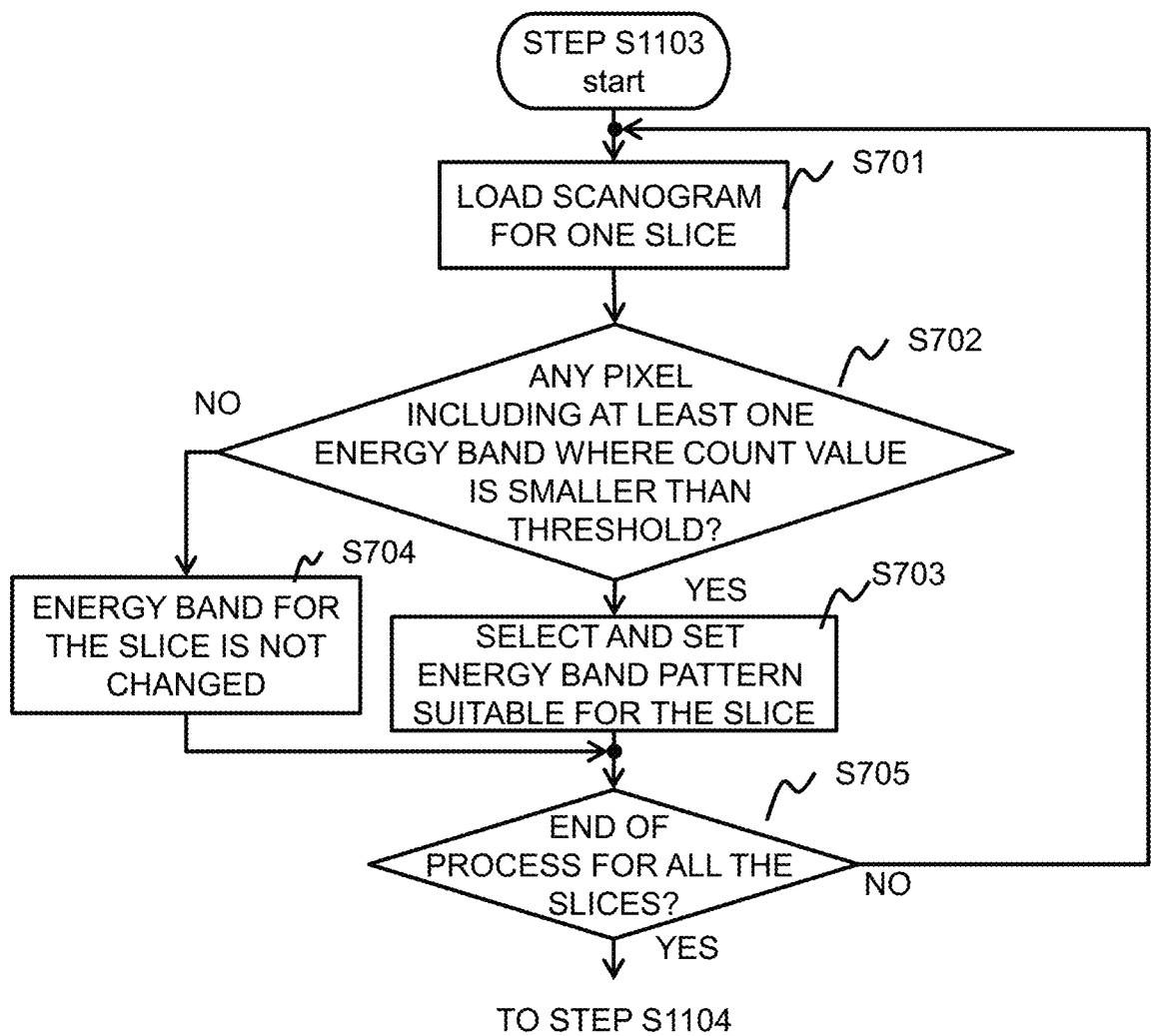
FIG. 7 is a flowchart showing in detail a part of the flowchart of FIG. 6.

With reference to the processing flow of FIG. 7, there will be described the step S1103 in detail. The energy band setter 404 loads a scanogram for one slice, from the scanograms stored in the HDD 403 (the distribution of degrees of X-ray attenuation 40) (step S701). One-pixel data of the scanogram includes count data of the X-ray photons detected by one detecting element of the X-ray detector 321, as to each of the energy bands. By way of example, one-pixel data includes count values in five energy bands. The energy band setter 404 determines whether or not there is any pixel including at least one energy band where the count value is smaller than a threshold, in a plurality of pixels constituting the loaded one-slice scanogram (step S702). By way of example, in the case of a slice containing many bones or a slice where metal or a similar material are embedded into the subject, the degree of X-ray attenuation is high, and this reduces the count value in a low energy band (e.g., bin 1) to be lower than a predetermined threshold. If such pixel is included in the slice, the energy band setter 404 performs the step S703.

In step S703, the energy band setter 404 selects a pattern where the energy width of the energy band having the count lower than the threshold, is larger than the energy width provided at the time of scanogram imaging, out of the energy band patterns stored in the HDD 403. For example, in the case where the pattern of the energy bands upon the scanogram imaging corresponds to the pattern where the energy range from 40 to 140 is divided equally into five bins from 1 to 5, like the band pattern 3 shown in FIG. 3(*b*), when the count value in the bin 1 is lower than the threshold, the energy band setter 404 selects a pattern of the energy bands where only the energy width of bin 1 is enlarged and the remaining widths are made narrower, from the patterns stored in the HDD 403. In the example of FIG. 3(*b*), the energy band patterns 1, 2, and 4 include the bin 1 with the energy width larger than the remaining bins 2 to 5. Therefore, out of those patterns, an appropriate energy band pattern is selected so that the count values in all the bins 1 to 5 become equal to or larger than a predetermined value, in response to data of the scanogram such as the count value in the bin 1. In this example, the energy band setter 404 selects the energy band pattern 4.

There may be some methods for selecting the energy band pattern, including a method where a predetermined energy band pattern is selected in response to the count value in the bin 1, and a method that obtains estimated counts in the bins 1 to 5 by using predefined equations, or the like, for the case where selectable energy band patterns 1, 2, or 4 is set on the basis of the count values in the bins 1 to 5. In this method, the energy band pattern is selected in a manner that the estimated counts in the bins 1 to 5 become equal to or larger than a predetermined value, or the counts in the respective energy bands become values close to each other.

On the other hand, in step S702, when all the plurality of pixels constituting the loaded scanogram for one slice, have the count values in the energy bands, larger than the threshold, the energy band setter 404 performs the step S704 next, and keeps the same energy band pattern for the slice as the pattern provided at the time of obtaining the scanogram, without changing the energy band pattern (step S704).

The energy band setter 404 performs the aforementioned steps from S701 to S704, as to each of all the slices (step S705). This allows the energy band setter 404 to provide an optimum energy band pattern as to each of the slices in the z-direction. For example, as shown in FIG. 3 (*a*), for the section (region) including many bones 41 and the section (region) embedded with metals 42, the energy band pattern 4 including the bin 1 with a large energy width is provided, and the energy band pattern 3 equally divided is set for the other sections.

Preferably, the energy band setter 404 has a configuration where a screen is created for presenting an operator a distribution of the energy band patterns provided as shown in FIG. 3 (*a*), the screen is displayed on the monitor of the UI unit 200, and the operator's confirmation is accepted by manipulating the buttons of the input device 210.

In step S702, instead of comparing the count value as to each of the energy bands with the threshold, the energy band setter 404 may proceed with the step S703, when a minimum count among the count values in the respective energy bands indicates a ratio smaller than a predetermined ratio, relative to another count value (e.g., a maximum value and an average value).

In the subsequent step 1104, the correction unit 406 reads out from the HDD 403, data used for correction in the step S1106 described below, and stores thus readout data in the memory 402 (step S1104). The HDD 403 stores in advance, the data used for correction, which is previously obtained as to each type of the energy band patterns (band patterns 1 to 4). In the example as shown in FIG. 3 (*a*), there are provided two types of the energy band patterns (band patterns 3 and 4), and thus, there is loaded the correction data that is required for correcting the values obtained by counting the X-ray photons in the two types of energy band patterns. The loaded correction data is, for example, an X-ray attenuation coefficient of a reference substance in each energy band, which is required for discriminating the reference substance constituting the subject 101, on the basis of the count data of each energy band. In addition, there may be loaded a correction coefficient used in performing a publicly-known water-phantom calibration for correcting the count value, in response to the size of the subject, and correction data for correcting a CT value, and the like, as required. Such correction data may be obtained by actual measurement in advance, or by calculation.

Next, the imager 405 executes the PCCT imaging, with the imaging conditions set in the step S1101 and the energy bands provided in the step S1103 (step S1105).

There will be described specifically a process for imaging a CT image according to photon counting. The imager 405 instructs the table controller 343 to move the table 102 in the direction vertical to the rotating plane of the rotating panel 332, and to stop the movement when the imaging position of the rotating panel 332 coincides with a designated imaging position. Then, positioning of the subject 101 is completed. Next, the imager 405 instructs the gantry controller 342 to start rotation of the rotating panel 332. When the rotating panel 332 starts constant-speed rotation, the imager 405 instructs the radiation controller 341 a timing for applying X-rays from the X-ray tube 311, and instructs the detection controller 344 a timing for delivering data counted by the X-ray detector 321 to the arithmetic unit 400. Then, X-ray irradiation and outputting of a result of X-ray photon counting according to the X-ray detector 321 are performed every 1 ms, for instance. The X-ray photons passing through the subject are discriminated into the energy bands, in response the energy levels of the X-ray photons, at every predetermined angles (views) per rotation, and the count values are obtained.

After the count data of each view is acquired on the imaging position, the imager 405 instructs the table controller 343 to perform actions, and the operation for acquiring the count data of each view in one rotation of the rotating panel 332 is repeated across the entire imaging area in the z-direction.

At this time, the energy band setter 404 sets in the counting circuit 324 of the X-ray detector 321, energy bands of the energy band pattern provided to the slice of the imaging position in the step S1103, every time the table 102 moves to each imaging position (each position in the z-direction). By way of example, the energy band setter 404 sets the band pattern 3, to the slices 1 to 64, the slices 112 to 144, and the slices 200 to 256, in the case of 256 slices, and sets the band pattern 4 to the section (region) 41 corresponding to the slices 65 to 111, and to the section (region) 42 corresponding to the slices 145 to 199. Specifically, the energy band setter 404 sets the comparative voltage of the multiple comparators 22 (22a, 22b, and so on) in FIG. 4, as boundary voltage between each of the energy bands (bins 1 to 5) of the band pattern being provided (indicating the band patterns 3 and 4 in FIG. 3(a)).

As described above, the energy band setter 404 provides an optimum energy band for each slice, whereby even when the degree of X-ray attenuation of the slice is high, the count value in the energy band (bin) is not made too small, and it is less likely to be affected by noise.

The imager 405 may control imaging, in a manner that imaging is performed with rotation of the rotating panel 332, while moving the table 102 continuously, like a publicly-known helical scan. In the helical scan, when the position of the X-ray detector 321 in the z-axis (body axis) direction reaches a certain distance (reaches an imaging position), the energy band setter 404 switches the setting of the energy band pattern, whereby the energy range can be provided in the slice direction.

The correction unit 406 corrects the count data that the arithmetic unit 400 has received from the X-ray detector 321 (step S1106). At this time, the correction unit 406 performs correction using the correction data that is loaded previously as to each of the energy band patterns in the step S1104, enabling correction to be performed appropriately in response to the range of the energy band. The correction unit 406 may perform the correction process on the count data as it is. Alternatively, the count data may be once converted into distance information of a base substance, and the correction process is performed on the converted information. It is to be noted that in step S1104, the correction data is loaded and stored in the memory 402 in advance, and thus this allows reduction of the time required for the correction process.

The image generator 407 generates an image using thus corrected data (step S1107). Further at this stage, the correction data loaded in step S1104 may be used as appropriate, to generate the image. The image generator 407 stores the image generated in step S1107 in the HDD unit 403, and displays the image on the monitor of the output device 220 in the UI unit 200 (step S1108). According to the procedures so far, the sequence of imaging is completed. Then, the user may use the image for diagnosis and perform image analysis as appropriate.

As discussed so far, in the PCCT device of the present embodiment, a scanogram is obtained or a similar process is performed, so as to provide multiple energy bands optimally on the basis of the previously obtained distribution of degrees of X-ray attenuation 40. Therefore, even though there are portions including many bones or embedded with metal within the subject 101, the count values in the energy bands (bins) can be prevented from becoming smaller than the threshold. Therefore, just one time photon-counting CT imaging reliably enables displaying of an image less affected by noise.

In addition, the PCCT device of the present embodiment changes the energy width of the energy band (bin), but not the number of energy bands. Therefore, it is possible to set the number of energy band to a minimum required number, and this allows minimization of wiring number between the X-ray detector 321 on the rotating panel 332, and the arithmetic unit 400. Therefore, even with this simple configuration, the device can be less affected by noise.

In the present embodiment, in step S1103, the energy band setter 404 selects an energy band pattern so that the minimum count value in the energy bands (bins 1 to 5) becomes equal to or larger than the threshold. However, the energy band may be changed to a different range, according to different criteria.

Modification Example 1

In the present embodiment, a scanogram is obtained only once in the imaging process flow in FIG. 6, but the scanograms may be obtained respectively from a plurality of directions. By using count data (scanograms) acquired as to each of the energy bands respectively from the plurality of directions, Tomosynthesis process is performed on each energy band, whereby a two-dimensional image (Tomosynthesis image) for each of the energy bands may be reconstructed. Accordingly, the energy band setter 404 is now able to set optimum energy bands, by using the Tomosynthesis image as to each of the energy bands.

Figure 8:
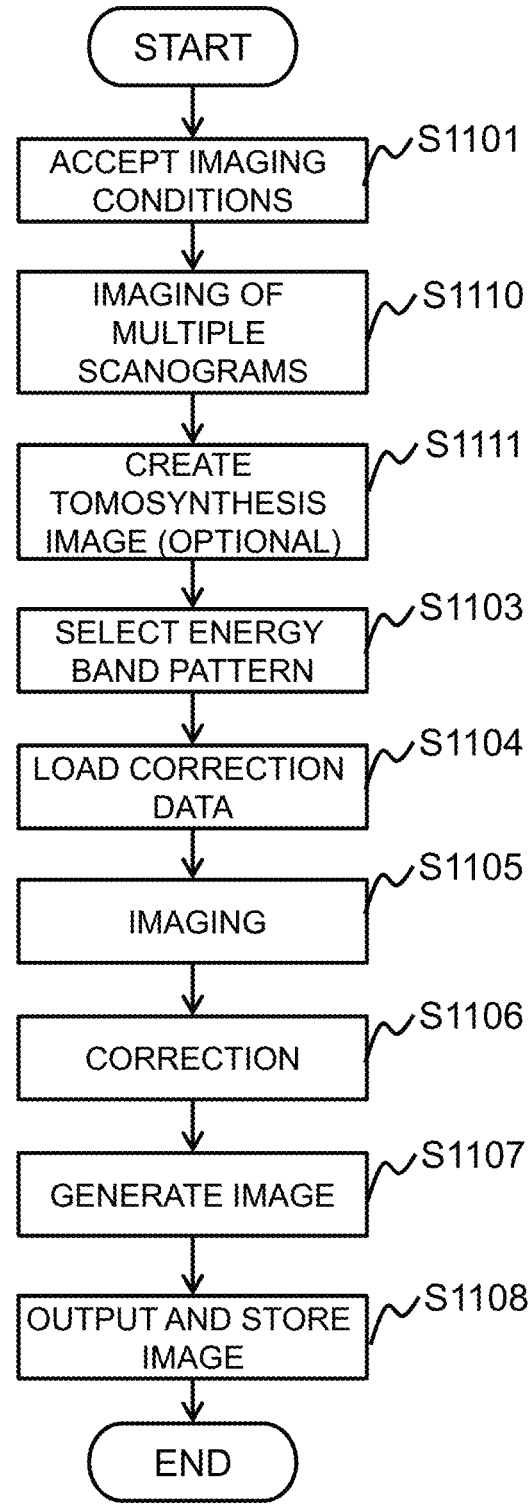
FIG. 8 is a flowchart showing the imaging process of a first modification example of the present embodiment.

FIG. 8 is a flowchart of the imaging process when the Tomosynthesis image is reconstructed. The process flow of FIG. 8 is different from the process flow of FIG. 6, in the point that the steps of S1110 and S1111 are executed instead of the S1102 in FIG. 6. In step S1110, the imager 405 instructs the gantry controller 342 to slant the rotating panel 332 at a predetermined rotation angle, and count values as to each of the energy bands are obtained in a plurality of directions, thereby taking scanograms. In step S1111, the imager 405 allows the image generator 407 to create the Tomosynthesis image as to each of the energy bands, as required.

In step S1103, the energy band setter 404 measures, using the Tomosynthesis image, an area and a shape of metal or a similar material within a body, and distance from the X-ray emitter 310 and from the X-ray detector 321, and an energy band pattern may be selected on the basis of one or more of those information items. With this configuration, setting of the energy bands can be performed with a high degree of precision, enabling improvement of an image quality.

Other steps in FIG. 8 are the same as those as shown in FIG. 6, and thus they will not be described redundantly. It is to be noted that a low-current CT imaging may be performed to obtain a low-current CT image, and the low-current CT image may be used in the same manner as described above, instead of the Tomosynthesis image.

Modification Example 2

Figure 9:
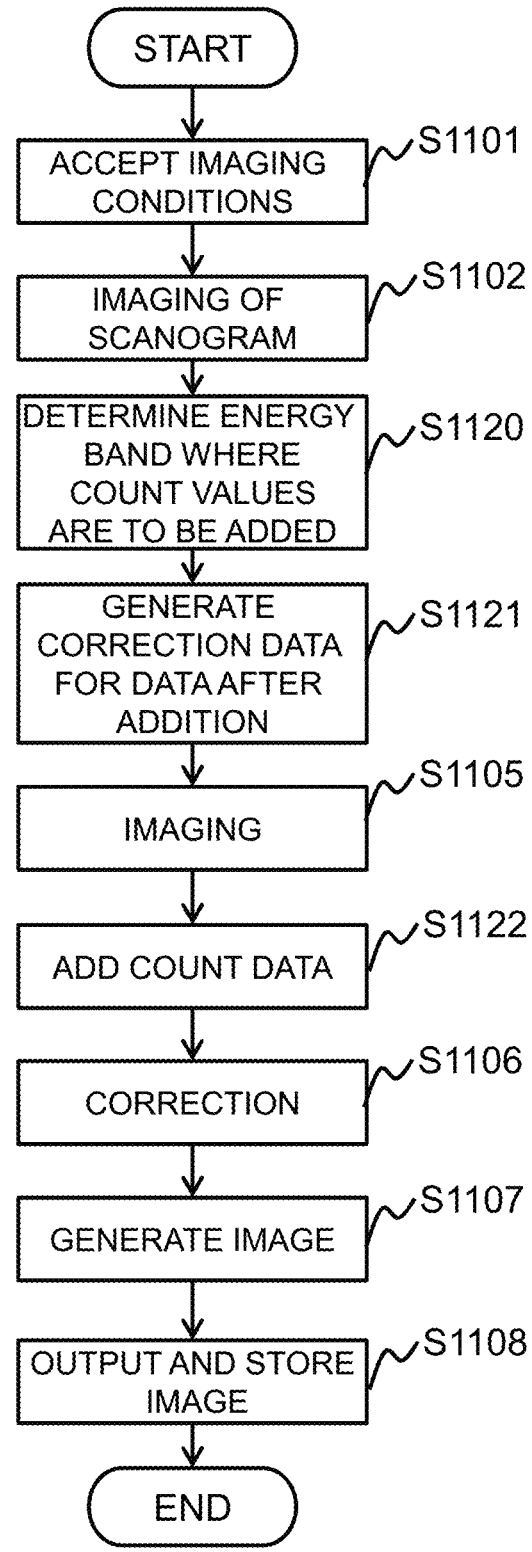
FIG. 9 is a flowchart showing the imaging process of a second modification example of the present embodiment.

In the aforementioned embodiment, in the step S1103 of the imaging process shown in FIG. 6, the energy band setter 404 changes the energy width itself of the energy band, according to the previously obtained distribution of the degrees of X-ray attenuation. In the configuration of this example, the count value in an energy band is added to the count value in another energy band. FIG. 9 is a flowchart of the imaging process in the case above.

In the process flow as shown in FIG. 9, the step S1120 for determining how to add data in the energy bands, and the step S1121 for generating correction data for the data after the addition is performed, instead of the step S1103 for selecting an energy band pattern and the step S1104 for loading the correction data in the process flow in FIG. 6. After the step of imaging S1105, the step of data addition (step S1122) is further provided.

The steps S1101 and S1102 are performed in the same manner as the aforementioned embodiment, and a scanogram is acquired. In the step S1120, the energy band setter 404 detects variability of count values in all the energy bands, according to the count data of the scanogram. Then, a method for adding (combining) the count values in two or more adjacent energy bands is considered to reduce the variability of the count values in all the energy bands, and a combination of energy bands is determined for minimizing the variability of the overall count values by the addition (step S1120). For example, the combination of energy bands targeted for the addition may be determined, so that uniform standard deviation SD can be obtained.

The combination of the energy bands targeted for the addition may be changed in the z-axis (body axis) direction, as in the case of the aforementioned embodiment.

Next, after the count values in two or more energy bands are added in the step S1120, the correction unit 406 generates correction data according to predetermined arithmetic computations, correction data being required for correcting the count value after the addition (step S1121). The step S1121 may be performed prior to the imaging in step S1105, or in parallel thereto.

Thereafter, in step S1105, imaging is performed similar to the aforementioned embodiment. After the imaging, in the step S1122, the energy band setter 404 adds up the count values in two or more energy bands according to the addition method defined in step S1120. In the step S1106, the correction unit 406 performs the correction process on the count values after the addition, by using the correction data obtained in the step S1121. The image generation process in step S1107 and the image outputting and storing process in S1108, performed subsequently, are the same as those described in the aforementioned embodiments.

In the present modification example, the count values in two or more energy bands are added, thereby suppressing the statistical noise on the low count side. Therefore, an image less affected by noise can be obtained.

The imaging method of the present modification example determines two or more energy bands for adding the count values, on the basis of the distribution of the degrees of X-ray attenuation, which is acquired by scanogram imaging. Therefore, immediately after the count values are obtained by the imaging in the step S1105, addition is performed using an optimum combination, and then an image is generated. This enables displaying for the user in a short time, an image where noise has been reduced. Since correction data is calculated in step S1121 prior to the imaging, the correction process can be performed on the data obtained by the addition, immediately after the imaging.

Modification Example 3

In the aforementioned embodiments, when the correction unit 406 performs the correction process on the count data as it is in the step S1106, a boundary between the sections where different energy band patterns are provided respectively, may cause that different energy band patterns are set even in the adjacent slices in the body axis (z-axis) direction of the subject 101. Accordingly, the image generator creates images in the step S1107, using the values counted respectively in the energy bands with different energy widths. Therefore, there is a possibility that images may be affected on the boundary between the different energy band patterns.

Figure 10:
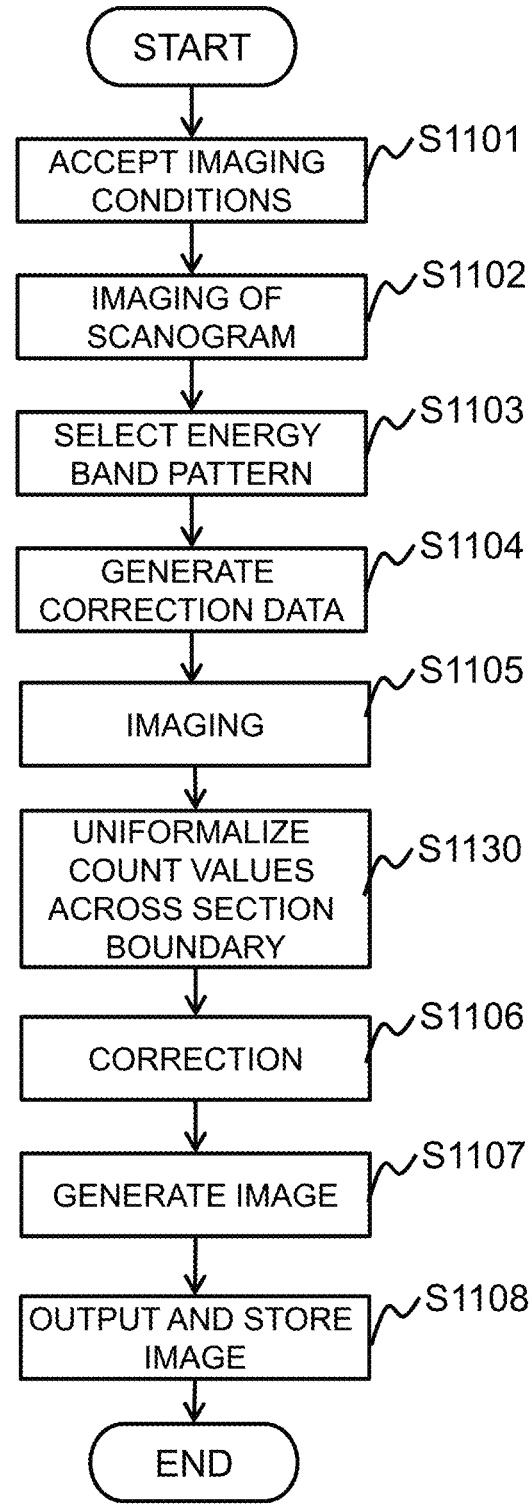
FIG. 10 is a flowchart showing the imaging process of a third modification example of the present embodiment.

In the present modification example, averaging process is performed on the count values, so that the images may be less affected by the different energy band patterns placing the boundary therebetween, for the slices near the boundary between the sections where different energy band patterns are provided respectively in the body axis (z-axis) direction. FIG. 10 shows the flowchart for the case above.

As shown in FIG. 10, subsequent to the imaging in the step S1105, step S1130 is provided. In the step S1130, the count values in the energy bands with different patterns, respectively of two slices placing the boundary therebetween, are weighted and then added up, as to the corresponding energy bands (e.g., bins 1). The correction process (S1106) and the image generation process (S1107) are performed on the count values after added up, in the same manner as the aforementioned embodiments.

Accordingly, it is possible to prevent the image from being affected on the boundary between the different energy band patterns in the body axis (z-axis) direction, in addition to the reduction of noise occurrence due to small count values, enabling uniform images to be outputted.

In the present modification example, the count values immediately after the imaging in the step S1130 are weighted and added up. However, weighting and adding up may be performed in any timing, such as after the correction of step S1106, as far as the correction process maintains integrity.

Modification Example 4

In the present modification example, there will be described another processing method, which is different from the modification example 3, for preventing the images from being affected on the boundary between the sections where the different energy band patterns are provided in the body axis (z-axis) direction of the subject 101.

As described in the step S1106 of the aforementioned embodiment, the count data may be once converted into distance information of a base substance by the correction unit 406 (hereinafter, referred to as conversion to substance). The conversion to substance is performed in step S1106, and further if the conversion method is applied independently to individual projection data items (data of the detector at certain angles), the count information (count values) can be converted into distance information of a reference substance according to the conversion to substance. After all the data items are converted into the distance information of the reference substance, an image may be constructed from the distance information data of the reference substance, or on the contrary, count values may be calculated from the distance information of the reference substance, or the distance information may be converted to information of X-ray attenuation information. By use of those characteristics, even when different energy band patterns are set respectively in a plurality of sections in the body axis (z-axis) direction, or in the circumferential direction (x-direction), individual projection data items are once converted into the reference substance information, thereby obtaining uniform type of data. Therefore, count values in the energy bands of an energy band pattern that is different from the provided energy band pattern, can be obtained by computations, so as to reconstruct or correct the image. Consequently, on the boundary between different energy band patterns, it is possible to perform image generation or others, not affected by noise due to the count value equal to or less than a threshold, even with the setting of the energy bands of a unique type in the entire range, without an impact on a reconstructed image.

Figure 11:
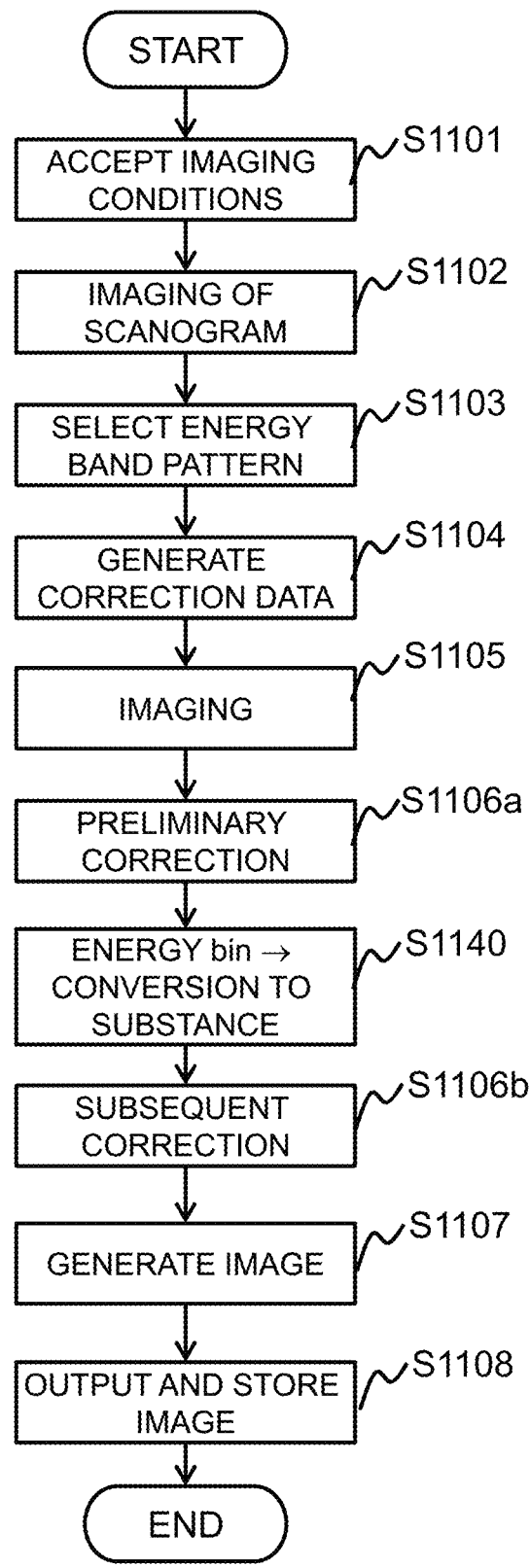
FIG. 11 is a flowchart showing the imaging process of a fourth modification example C the present embodiment.

With reference to the flowchart of FIG. 11, there will be described an imaging process in detail in the case where the conversion to substance is performed according to the present modification example. As illustrated in FIG. 11, the conversion to substance S1140 is performed after the imaging in step 1105. The correction process 1106 in the flowchart of FIG. 6 is divided into preliminary correction 1106a that is performed prior to the conversion to substance in step S1140 and the correction 1106b that is performed subsequent to the conversion to substance. By way of example, a correction such as phantom calibration correction that is applied to energy information may preferably be performed as the preliminary correction 1106a. In addition, a correction such as smoothing may preferably be performed as the correction subsequent to the conversion to substance 1106b. It should be noted, however, that correction equivalent to the phantom calibration may be performed after the conversion to substance, or correction such as smoothing may be performed prior to the conversion to substance.

There will be described an example of processing method for the conversion to substance in step S1140.

There will now be assumed that substances after the conversion are water, fat, and bone. Representative values of the energy ranges are also determined respectively. For example, it is assumed that the representative value of bin 1 (40 to 80 keV) is 60 keV, the representative value of bin 2 (80 to 95 keV) is 87.5 keV, the representative value of bin 3 (95 to 110 keV) is 102.5 keV, the representative value of bin 4 (110 to 125 keV) is 117.5 keV, and the representative value of bin 5 (125 to 140 keV) is 132.5 keV.

Attenuation coefficients of water, fat, and bone are obtained respectively, at each of the representative values. The attenuation coefficients are obtained at each of the representative values, by applying interpolation in the energy direction, to database values of attenuation coefficients of water, fat, and bone, which have been obtained every 10 keV, for instance. Next, there are obtained lengths of each of the substances (water, fat, and bone) existing between the X-ray source and the X-ray detector, on the basis of the respective attenuation coefficients, and X-ray signals (count values, air data) when there are no substances, as to each of the energy band bins 1 to 5. For example, when there are 10 mm of bone, 200 mm of water, and 50 mm of fat in length (distance), according to the respective attenuation coefficients for the representative value of each of the bins 1 to 5, in the range from the associated X-ray source to the X-ray detector, those distances can be considered as substance data after the conversion, if signal values of air data (the count values when there is no substance) can serve as measured signal values (count values). A specific conversion method will be described below. As for the bin 1, the representative value is 60 keV, and the total attenuation coefficient of water at 60 keV is $1.92 \times 10^{-1}$ cm$^2$/g. Since the density of water is 1 g/cm$^3$, the linear attenuation coefficient becomes 1.92 cm$^{-1}$. In other words, X-rays of 60 keV in the bin 1 is multiplied by exp $(-1.92^{-1} \times Lw)$, every Lw cm movement of the X-rays. Similar results can be obtained for the other substances and the other bins. Then, since there are three variables of lengths, i.e., bone, water, and fat, and imaging is performed at energy in the five bins, simultaneous equations are established, that is, five equations where lengths (distances) of three substances are unknown (three unknowns). By solving those equations, each length (distance) of the bone, water, and fat can be obtained as to each of paths (combinations of the X-ray source and the X-ray detector). As described above, signal values (count values) as to each of the energy bands; bins 1 to 5, are converted to distance indicating where each substance exists between the X-ray source to the X-ray detector. Consequently, projection data of the distance where each substance exists can be obtained, and thus when this data is reconstructed, it is possible to know where each substance exists. This is not the image reconstruction from the energy data (count data) as to each of the bins 1 to 5, but the image reconstruction from each of the substances. This means that an image can be reconstructed irrespective of the ranges of the energy bands (bins 1 to 5) where imaging is performed. With this configuration, even though the energy band pattern of the X-ray detector 321 is changed in any of the directions, the circumferential direction (x-direction) or the body-axis direction (z-direction), an image can be reconstructed.

In addition, by using the attenuation coefficients, data of each substance can also be converted into energy data (count data) in each of the energy bands. Consequently, in the overall ranges in the circumferential direction (x-direction) and in the body-axis direction (z-direction), image generation or others can be performed in a similar manner as the case where the X-ray detector 321 performs counting with the use of one type of energy band pattern.

Modification Example 5

In the aforementioned embodiments, as illustrated in FIGS. 3(a) and 3(b), the energy band setter 404 selects an optimum pattern, from predetermined multiple types of energy band patterns. In the present modification example, the energy band setter 404 adjusts each energy band freely in response to count values.

Figure 12:
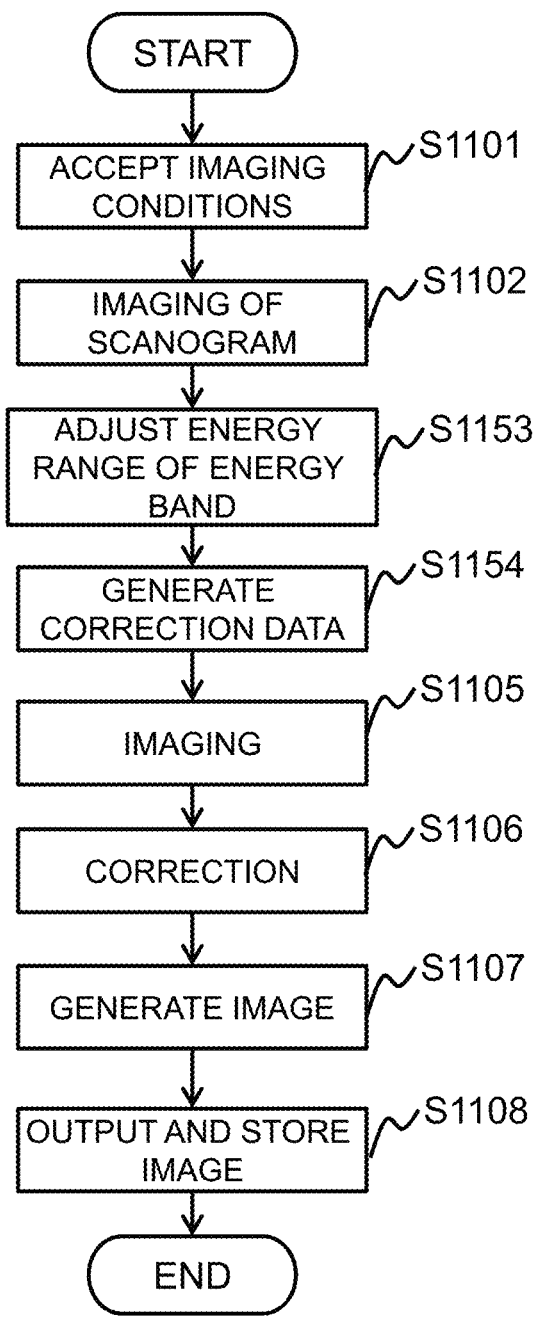
FIG. 12 is a flowchart showing the imaging process of a fifth modification example of the present embodiment.

FIG. 12 is a flowchart of the imaging process of the present modification example. Step S1153 for adjusting the energy range of the energy band and step S1154 for generating correction data, are performed instead of the step S1103 for energy band setting selection and the step S1104 for correction data loading in the flowchart of FIG. 6.

Firstly, in step S1102, a scanogram is obtained in the same manner as the aforementioned embodiments. Similar to the aforementioned embodiments, as the energy bands in the X-ray detector when obtaining the scanogram, the band pattern 3 as shown in FIG. 3(*b*) is provided, i.e., bin 1 (40 to 60 keV), bin 2 (60 to 80 keV), bin 3 (80 to 100 keV), bin 4 (100 to 120 keV), and bin 5 (120 to 140 keV).

In the step S1153, the energy band setter 404 sets (adjusts) the energy width (energy range) of each of the multiple energy bands, in a manner that the number of X-ray photons passing through the subject 101 and counted as to each of the multiple energy bands; bins 1 to 5, becomes uniform, on the basis of the scanogram (the distribution of the degrees of X-ray attenuation). By way of example, if the count values in the bin 1, bin 2, bin 3, bin 4, and bin 5 are 10, 100, 200, 100, 90, respectively, as a result of obtaining the scanogram, the total count is 500. Therefore, in step S1153, the energy band setter 404 assuming that the counts are equally distributed in each of the energy bands, the energy ranges of the energy bands are provided as the following; bin 1 (40 to 78 keV), bin (78 to 89 keV), bin 3 (89 to 99 keV), bin 4 (99 to 118 keV), and bin 5 (118 to 140 keV), respectively.

Next, the correction unit 406 generates correction data to be used in the steps S1106 and S1107 (step S1154). In the present modification example, the energy range of each of the energy bands (bins 1 to 5) is adjusted so that the counts in the respective energy bands become equivalent, and thus the correction data may become a value that is not included in the previously obtained correction data stored in the HDD 403 as described in the aforementioned embodiments. Therefore, in the present modification example, a plurality of correction data obtained in the embodiments is used and they are interpolated, whereby correction data is generated for the energy bands after the adjustment. For example, it is assumed that a group of five correction data items C1 to C5 is stored in the HDD 403 for correcting the counts respectively of the five energy bands; bin 1 (40 to 60 keV), bin 2 (60 to 80 keV), bin 3 (80 to 100 keV), bin 4 (100 to 120 keV), and bin 5 (120 to 140 keV) in the band pattern 3 of FIG. 3(*b*). The correction unit 406 generates the correction data for the bin 1 after the adjustment, by interpolating the correction data values for the bins 1 and 2 in the band pattern 3. For example, in the band pattern 3, the count value in the bin 1 (40 keV to 60 keV) is 10 (10 X-ray photons), and the count in the bin 2 (60 keV to 80 keV) is 100 (100 X-ray photons). However, since the newly provided bin 1 is (40 keV to 78 keV), the X-ray photons counted in the new bin 1 corresponds to all in the original bin 1 (10) and 90% of the original bin 2 (including a portion corresponding to 60 to 78 keV out of the original bin 2 corresponding to 60 to 80 keV). Therefore, in the new bin 1, the ratio between the count in the original bin 1 and the count from the bin 2 becomes 10:90. Accordingly, the correction data for the new bin 1 (40 to 78 keV) (after adjustment) is obtained by weighting the correction data C1 and C2 in association with the ratio of the count values, for example, by C1*0.1+C2*0.9. Similarly, in response to the ratio of the counts in the scanogram, the correction values C2 to C5 are weighted, whereby the correction data items for the bins 2 to 5 after the adjustment are calculated. In addition, since the energy range of the bin 3 (89 to 99 keV) after the adjustment is included in the energy range of the bin 3 of the band pattern 3 (80 to 100 keV), the correction data C3 for the bin 3 of the band pattern 3 (80 to 100 keV) can be used as it is.

Some other methods may be required for the correction by the correction unit 406, instead of the interpolation, and depending on the method thus employed, an optimum process will be performed as appropriate.

It should be noted that the narrower is the energy range of the previously obtained correction data stored in the HDD 403, the higher is the level of precision in interpolation. For example, if the correction data is generated every 1 keV, the correction data for the bin 1 after the adjustment (40 to 78 keV) may be obtained in a manner that (an average value of the correction data in the range from 40 to 60 keV)*0.1+(an average value of the correction data in the range from 60 to 78 keV)*0.9.

As described in the present modification example, the energy band setter 404 can adjust the energy range of each of the energy bands, in response to the count values in the scanogram, whereby the counts in the energy bands (bins 1 to 5) can be smoothed more. Accordingly, a combination of the process of the present modification example and the conversion to substance in the modification example 4, allows generation of reconstructed image data that includes less noise.

DESCRIPTION OF SYMBOLS

100: PCCT device, 101: subject, 102: table, 200: UI unit, 210: input device, 220: output device, 300: measurement unit, 310: X-ray emitter, 311: X-ray tube, 312: X-ray filter, 313: bowtie filter, 320: X-ray detect device, 321: X-ray detector, 322: detecting element, 323: collimator, 324: counting circuit, 330: gantry, 331: opening, 332: rotating panel, 340: controller, 341: radiation controller, 342: gantry controller, 343: table controller, 344: detection controller, 400: arithmetic unit, 401: central processing unit, 402: memory, 403: HDD unit, 404: energy band setter, 405: imager, 406: correction unit, 407: image generator

What is claimed is:

1. A photon-counting CT device, comprising,
    an X-ray emitter configured to irradiate a subject with X-rays,
    an X-ray detector configured to count a plurality of X-ray photons passing through the subject, with discriminating the X-ray photons into multiple energy bands in response to energy levels of the X-ray photons,
    a rotator configured to rotate the X-ray emitter and the X-ray detector around the subject, and
    an energy band setter configured to set the energy bands in the X-ray detector, wherein,
    the energy band setter sets an energy range of at least one of the multiple energy bands in the X-ray detector, on the basis of a distribution of degrees of X-ray attenuation at respective energy levels, the distribution being measured in advance with respect to a predetermined direction of the subject.

2. The photon-counting CT device according to claim 1, wherein,
    the X-ray emitter irradiates the subject with the X-rays without rotating the rotator, and the X-ray detector with predetermined values of energy ranges respectively for the multiple energy bands, counts the X-ray photons passing through the subject, thereby obtaining the distribution of degrees of X-ray attenuation.

3. The photon-counting CT device according to claim 1, wherein,
    when the distribution of degrees of X-ray attenuation includes an energy level where the degree of X-ray attenuation is higher than a predetermined threshold, the energy band setter expands an energy width of the energy band including the energy level, to be larger than the energy widths of remaining energy bands.

4. The photon-counting CT device according to claim 2, wherein,
when the distribution of degrees of X-ray attenuation includes an energy level where the degree of X-ray attenuation is higher than a predetermined threshold, the energy band setter expands an energy width of the energy band including the energy level, to be larger than the energy width of the energy band including that energy level, the energy width previously provided at the time of obtaining the distribution of degrees of X-ray attenuation.

5. The photon-counting CT device according to claim 1, wherein,
the energy band setter selects a set of energy bands from predetermined multiple types of energy band patterns, in response to the distribution of degrees of X-ray attenuation, and provides the X-ray detector with the set of energy bands, as the multiple energy bands.

6. The photon-counting CT device according to claim 1, wherein,
the X-ray detector comprises a plurality of detecting elements configured to detect the X-ray photons and to output electrical signals in response to energy levels of the X-ray photons, and counter circuits each configured to discriminate the electrical signals into multiple energy bands in response to the energy levels, and to count the signals as to each of the energy bands, and
the energy band setter sets the multiple energy bands in the counter circuit.

7. The photon-counting CT device according to claim 1, further comprising a movable unit configured to move the subject in the direction crossing a rotating plane of the rotator, wherein,
the energy band setter sets multiple sections in the moving direction of the movable unit, and further sets, respectively in the multiple sections, different widths of energy range for at least one of the multiple energy bands.

8. The photon-counting CT device according to claim 1, wherein,
the energy band setter changes the energy range of at least one energy band, among the multiple energy bands, in response to a rotation angle of the rotator.

9. The photon-counting CT device according to claim 2, wherein,
the energy band setter sets in the X-ray detector, the energy bands the number of which corresponds to the number of energy bands that are provided when the distribution of degrees of X-ray attenuation is obtained.

10. The photon-counting CT device according to claim 2, further comprising an imager configured to generate an image of the distribution of degrees of X-ray attenuation, wherein,
the imager irradiates the subject with X-rays from a predetermined direction without rotating the rotator, and performs imaging for counting the X-ray photons passing through the subject by the X-ray detector, on the subject from a plurality of directions, creates a Tomosynthesis image using count data thus obtained, and uses the Tomosynthesis image as the distribution of degrees of X-ray attenuation.

11. The photon-counting CT device according to claim 3, wherein,
when the distribution of degrees of X-ray attenuation includes an energy level where the degree of X-ray attenuation is larger than a predetermined threshold, the energy band setter determines to add a count value to another count value in one or more adjacent energy band, so as to enlarge the energy width of the energy band that includes the energy level.

12. The photon-counting CT device according to claim 7, wherein,
the energy band setter performs averaging of count values respectively in corresponding energy bands, the count values being obtained as to each of the energy bands in regions respectively of the multiple sections near a boundary, the regions placing the boundary therebetween.

13. The photon-counting CT device according to claim 1, further comprising a conversion-to-substance unit configured to use count data obtained by the X-ray detector as to each of the multiple energy bands, with rotation of the rotator for rotating the X-ray emitter and the X-ray detector, so as to convert the count data into distance information of at least one predetermined base substance.

14. The photon-counting CT device according to claim 1, wherein,
the energy band setter sets the energy widths of the multiple energy bands respectively, so that the number of X-ray photons in each of the energy bands becomes uniform, on the basis of the distribution of degrees of X-ray attenuation, the X-ray photons passing through the subject and counted as to each of the multiple energy bands.

15. The photon-counting CT device according to claim 14, further comprising a correction unit configured to correct a count value of the X-ray photons counted as to each of the multiple energy bands, by using correction data, wherein,
the correction unit uses previously obtained correction data as to each of predetermined energy bands, and obtains the correction data by computations, to be used for correcting the count value as to each of the energy bands that are provided by the energy band setter.

16. A CT imaging method by using photon counting, comprising,
irradiating a subject with X-rays without rotating an X-ray emitter and an X-ray detector around the subject, counting by the X-ray detector, X-ray photons passing through the subject as to each of predetermined multiple energy bands, thereby obtaining a distribution of degrees of X-ray attenuation,
adjusting an energy range of at least one of the multiple energy bands in the X-ray detector, on the basis of the distribution of degrees of X-ray attenuation,
irradiating the subject with X-rays while rotating the X-ray emitter and the X-ray detector around the subject, and counting by the X-ray detector, the X-ray photons passing through the subject, as to each of the predetermined multiple energy bands, and
reconstructing an image of the subject by using a result of the counting.

* * * * *